(12) United States Patent
Uhland et al.

(10) Patent No.: US 8,642,830 B2
(45) Date of Patent: Feb. 4, 2014

(54) DRUG DEACTIVATION METHOD

(75) Inventors: Scott Albert Uhland, Redwood City, CA (US); Eric Peeters, Mountain View, CA (US); Francisco E. Torres, San Jose, CA (US); Philipp Helmut Schmaelzle, Los Altos, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 0 days.

(21) Appl. No.: 13/541,607

(22) Filed: Jul. 3, 2012

(65) Prior Publication Data

US 2012/0277514 A1    Nov. 1, 2012

Related U.S. Application Data

(62) Division of application No. 12/357,224, filed on Jan. 21, 2009, now Pat. No. 8,236,238.

(51) Int. Cl.
*A62D 3/10*    (2007.01)

(52) U.S. Cl.
USPC .......................................... 588/301; 588/410

(58) Field of Classification Search
USPC .............. 588/249.5, 402, 900, 405, 410, 301, 588/306
See application file for complete search history.

(56) References Cited

U.S. PATENT DOCUMENTS

| | | | |
|---|---|---|---|
| 5,985,101 A | 11/1999 | Kagitani | |
| 6,491,666 B1 | 12/2002 | Santini, Jr. et al. | |
| 6,527,762 B1 | 3/2003 | Santini, Jr. et al. | |
| 6,537,256 B2 | 3/2003 | Santini, Jr. et al. | |
| 6,669,683 B2 | 12/2003 | Santini, Jr. et al. | |
| 6,730,072 B2 | 5/2004 | Shawgo et al. | |
| 6,827,250 B2 | 12/2004 | Uhland et al. | |
| 6,875,208 B2 | 4/2005 | Santini, Jr. et al. | |
| 7,041,130 B2 | 5/2006 | Santini, Jr. et al. | |
| 7,052,488 B2 | 5/2006 | Uhland | |
| 7,070,592 B2 | 7/2006 | Santini, Jr. et al. | |
| 7,114,312 B2 | 10/2006 | Coppeta et al. | |
| 7,410,616 B2 | 8/2008 | Santini, Jr. et al. | |
| 7,413,846 B2 | 8/2008 | Maloney et al. | |
| 2002/0151776 A1 | 10/2002 | Shawgo et al. | |
| 2002/0173745 A1 | 11/2002 | Santini, Jr. et al. | |
| 2002/0183721 A1 | 12/2002 | Santini, Jr. et al. | |
| 2003/0010808 A1 | 1/2003 | Uhland et al. | |
| 2003/0021722 A1 | 1/2003 | Allen et al. | |
| 2003/0105455 A1 | 6/2003 | Santini, Jr. et al. | |
| 2004/0034332 A1 | 2/2004 | Uhland | |
| 2004/0143236 A1 | 7/2004 | Santini, Jr. et al. | |
| 2004/0247671 A1 | 12/2004 | Prescott et al. | |
| 2005/0048086 A1 | 3/2005 | Flashner-Barak et al. | |
| 2005/0050859 A1 | 3/2005 | Coppeta et al. | |
| 2005/0077584 A1 | 4/2005 | Uhland et al. | |
| 2005/0163717 A1 | 7/2005 | Anderson et al. | |
| 2005/0278015 A1 | 12/2005 | Dave et al. | |
| 2006/0024358 A1 | 2/2006 | Santini, Jr. et al. | |
| 2006/0057737 A1 | 3/2006 | Santini, Jr. et al. | |
| 2006/0173514 A1 | 8/2006 | Biel et al. | |
| 2007/0016163 A1 | 1/2007 | Santini, Jr. et al. | |
| 2007/0036835 A1 | 2/2007 | Coppeta et al. | |
| 2008/0015494 A1 | 1/2008 | Santini, Jr. et al. | |
| 2008/0033260 A1 | 2/2008 | Sheppard et al. | |
| 2008/0075669 A1 | 3/2008 | Soscia et al. | |
| 2008/0076975 A1 | 3/2008 | Santini, Jr. et al. | |
| 2008/0217447 A1 | 9/2008 | Jeansonne et al. | |

FOREIGN PATENT DOCUMENTS

| | | |
|---|---|---|
| EP | 1593374 | 11/2005 |
| WO | 2004093801 | 11/2004 |
| WO | 2006133733 | 12/2006 |

OTHER PUBLICATIONS

European Search Report dated Jun. 22, 2010 corresponding to European Application No. 10151233.3.
Calza et al., "Study of the photolytic and photocatalytic transformation of amiloride in water", Journal of Pharmaceutical and Biomedical Analysis, Sep. 29, 2008, pp. 315-320.
European Search Report dated Jun. 21, 2010 corresponding to European Application No. 10151232.5.

*Primary Examiner* — Edward Johnson
(74) *Attorney, Agent, or Firm* — Marger Johnson & McCollom PC

(57) ABSTRACT

A drug deactivation system according to some embodiments includes at least one drug-retaining region of a drug delivery device and at least one energy source coupled to the at least one drug-retaining region. The at least one drug-retaining region may be configured to retain a drug. The at least one energy source may be configured to transmit energy to the drug. The drug is capable of being rendered ineffective in the presence of the transmitted energy.

6 Claims, 5 Drawing Sheets

DRUG DEACTIVATION METHOD

RELATED CASES

This application is a divisional of, and claims priority to U.S. patent application Ser. No. 12/357,724, titles "DRUG DEACTIVATION SYSTEM," filed Jan. 21, 2009, now allowed.

TECHNICAL FIELD

Embodiments exemplarily described herein are generally related to systems configured to deactivate drugs, more particularly, to a drug deactivation system configured to render a drug within a drug-retaining region of a drug delivery device ineffective.

BACKGROUND

Generally, drug delivery devices (such as inhalers, syringes, intravenous bags, implantable drug delivery systems, transdermal patches, pill bottles, liquid medicine bottles, eyedroppers, etc.) store drugs until the drugs are required by a user. There are numerous occasions when it would be desirable to render the drugs contained within such drug delivery devices ineffective either automatically or manually in order to prevent the drug from being improperly released into the public (e.g., though the public water supply, through the garbage, etc.) or improperly obtained (e.g., through tampering of the drug delivery device).

It was the understanding and recognition of these and other problems associated with the conventional art that formed the impetus for the embodiments exemplarily described herein.

DETAILED DESCRIPTION OF THE EMBODIMENTS

Figure 1A:
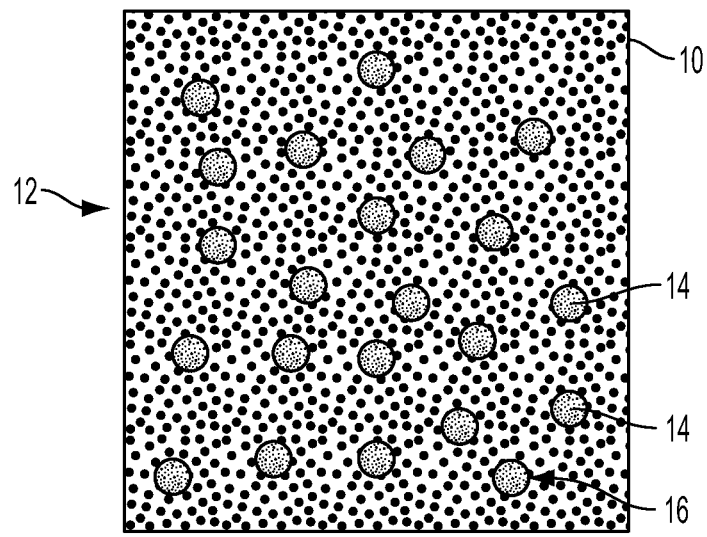
FIGS. 1A and 1B are plan views schematically illustrating an exemplary embodiment of a drug deactivation system according to an embodiment.
Figure 1B:
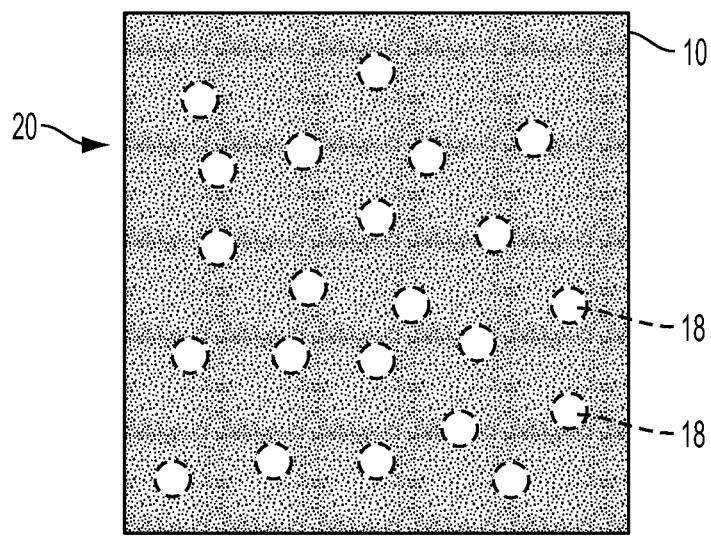

FIGS. 1A and 1B are plan views schematically illustrating an exemplary embodiment of a drug deactivation system according to an embodiment.

Referring to FIG. 1A, a drug deactivation system may be implemented with a drug delivery device including a drug-retaining region 10 within which a drug 12 is retained. The drug delivery device may be provided as an inhaler, a syringe, an intravenous bag, an implantable drug delivery system, a transdermal patch, a pill bottle, a liquid medicine bottle, an eyedropper, or the like or a combination thereof. An exemplary discussion of drug delivery devices capable of use with the embodiments disclosed herein can be found in co-pending U.S. patent application Ser. No. 12/357,108 filed Jan. 21, 2009, now U.S. Pat. No. 7,838,715, entitled "DRUG DEACTIVATION SYSTEM AND METHOD OF DEACTIVATING A DRUG USING THE SAME," the disclosure of which is incorporated herein by reference in its entirety. Accordingly, a drug delivery device may, for example, include a housing within which the drug-retaining region is located.

As will be exemplarily described in greater detail below, the drug 12 may be rendered ineffective in the presence of an agent. As used herein, the term "drug" refers to any material intended for use in the diagnosis, cure, mitigation, treatment, or prevention of disease in a human or other animal, or any material (other than food) which affects the structure or any function of the body of a human or other animal. Thus, a drug is rendered "ineffective" when its intended use is prevented from being realized by the user.

In the illustrated embodiment, the drug neutralization system may include a plurality of capsules 14 exposed to the drug-retaining region 10. The capsules 14 may be distributed throughout the drug-retaining region 10. Each of the capsules 14 may include a reservoir. An agent 16 may be retained within the reservoir of the capsule 14. As will be described in greater detail below, the capsules 14 are degradable. Accordingly, the agent 16 may be supplied to the drug 12 when the capsules 14 become degraded. The agent 16 is configured to render the drug 12 ineffective when the agent is supplied to the drug 12. However, when the capsules 14 are not degraded or are in a substantially non-degraded state, the agent 16 is isolated from the drug 12 so that the drug 12 is not rendered ineffective.

In the illustrated embodiment, the capsules 14 are the same shape and size. It will be appreciated, however, that the capsules 14 may have different shapes and/or sizes. In the illustrated embodiment, the capsules 14 are spherical. It will be appreciated, however, that the capsules 14 may have substantially any shape. It will also be appreciated that the number, size and shape of the capsules 14 exposed to the drug-retaining region 10 may be selected to ensure that a sufficient amount of agent 16 can be provided to render the drug 12 within the drug-retaining region 10 ineffective. Indeed, the capsules 14 may be replaced with a single capsule 14 retaining substantially the same amount of agent 16 as each of the capsules 14 combined.

Referring to FIG. 1B, the capsules 14 shown in FIG. 1A become degraded upon receiving energy supplied from an energy source, as will be described in greater detail below. Generally, however, energy capable of degrading the capsules 14 may include electrical energy, thermal energy, chemical energy, mechanical energy, electromagnetic radiation, magnetic energy, or the like or a combination thereof. The degraded capsules are identified at 18 with dashed lines to represent degradation of the material forming the capsules 14. As exemplarily illustrated, the capsules 14 are partially degraded to form degraded capsules 18. It will be appreciated, however, that at least some of the capsules 14 may be fully degraded, in which case the degraded capsules 18 would not exist.

When the capsules 14 are degraded, the agent 16 retained therein is released into the drug-retaining region 10. In one embodiment, agent 16 released from the degraded capsules 18 may migrate within the drug 12 via self-diffusion or forced-diffusion (e.g., within a chemical gradient, a force gradient, an electrical potential gradient, or the like or a combination thereof). Upon being released into the drug-retaining region 10, the agent renders the drug 12 shown in FIG. 1A ineffective. The ineffective drug is identified at 20. In one embodiment, the agent 16 binds to the drug 12 to render the drug 12 ineffective. In another embodiment, the agent 16 binds to receptors of the drug 12 to render the drug 12 ineffective. For example, the drug 12 could be morphine and the agent 16 could be cyprodime (an opioid receptor antagonist). In yet another embodiment, the agent 16 chemically degrades the drug 12 to render the drug 12 ineffective. For example, the drug 12 could be insulin and the agent 16 could be a strong acid or base. Table 1 identifies exemplary materials of which the agent 16 may be comprised, depending on some exemplary drugs that may be retained within the drug-retaining region 10.

TABLE 1

| Medical Application | Drug retained within drug-retaining region 10 | Agent 16 |
| --- | --- | --- |
| Pain management | morphine, codeine hydromorphone, hydrocodone, oxycodone, oxymorphone, desomorphine, diacetylmorphine, nicomorphine, dipropanoylmorphie, benzylmorphine, pethidine, methadone, tramadol, propoxyphene, endorphins, enkephalins, dynorphins, endomorphins. | Cyprodime, Naltrindole, Norbinaltorphimine, Hydrogen peroxide, metabolizing enzymes such as NADH and NADPH, caustic reactants, such as NAOH, KOH, trimethylamine |
| Antibiotics | Penicillin, cephalosporins, other β-lactam antibiotics, Aminoglycosidic antibiotics fluoroquinolones, nitrofurans, vancomycin, monobactams, co-trimoxazole, metronidazole | β-lactamase enzyme, strong acids, strong bases |
| anti-convulsants | Aldehydes, Aromatic allylic alcohols, Barbiturates, Benzodiazepines, Bromides, Carbamates, Carboxamides, Fatty acids, Fructose derivatives, Gaba analogs, Hydantoins, Oxazolidinediones, Propionates, Pyrimidinediones, Pyrrolidines, Succinimides, Sulfonamides, Triazines, Ureas, Valproylamides | Strong acids, strong bases |
| Reproductive Hormones | Amine-derived hormones: catecholamines, thyroxine; Peptide hormones: TRH, vasopressin; Protein hormones: insulin, growth hormone, luteinizing hormone, follicle-stimulating hormone, thyroid-stimulating hormone; testosterone, cortisol, calcitriol | Strong acids, strong bases, hydrolytic enzymes |

In one embodiment, at least one of the capsules 14 may be formed of a material capable of chemically binding with the agent 16. In such an embodiment, the material may be porous and may be degraded when supplied energy (e.g., electrical energy, mechanical energy, or the like or a combination thereof) overcomes a binding potential of the agent 16 to the porous material of the at least one of the capsules 14. In this manner, the at least one of the capsules 14 is "degraded" because it can no longer bind the agent 16 and can no longer retain the agent 16.

Figure 2A:
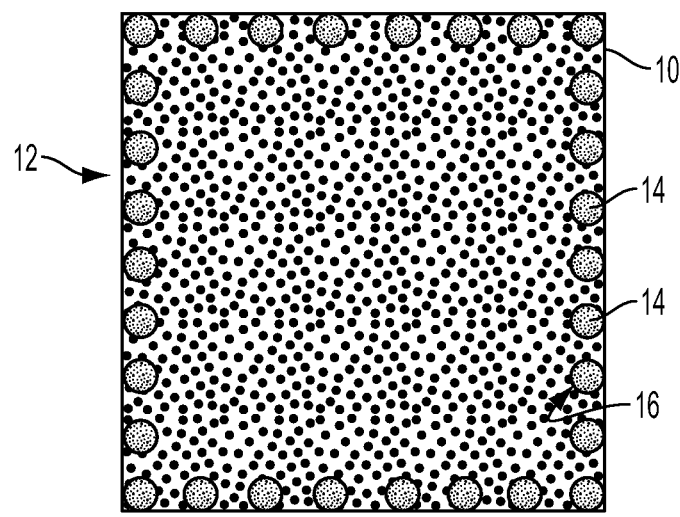
FIGS. 2A and 2B are plan views schematically illustrating another exemplary embodiment of a drug deactivation system according to another embodiment.
Figure 2B:
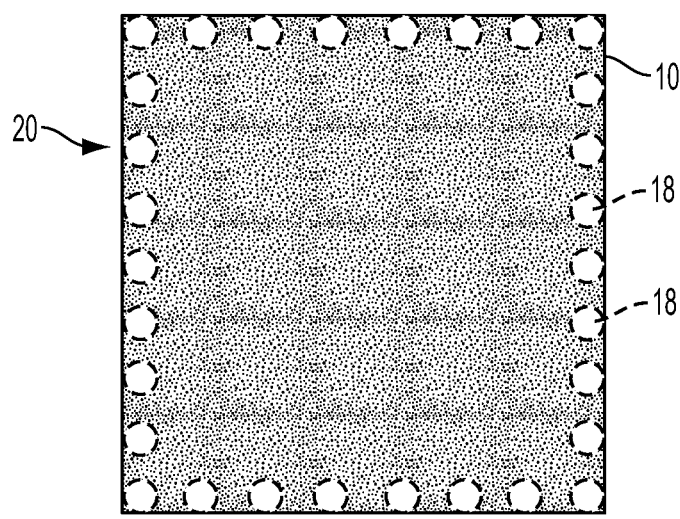

FIGS. 2A and 2B are plan views schematically illustrating an exemplary embodiment of a drug deactivation system according to another embodiment.

Referring to FIG. 2A, similar to the embodiment described above with respect to FIG. 1A, a drug deactivation system may be implemented with a drug delivery device including a drug-retaining region 10 within which a drug 12 is retained. The drug deactivation system may include a plurality of capsules 14 configured as exemplarily discussed above with respect to FIGS. 1A and 1B. The capsules 14 may retain an agent 16 therein, which is also configured as exemplarily discussed above with respect to FIGS. 1A and 1B. In the illustrated embodiment, however, the capsules 14 are distributed along the periphery of the drug-retaining region 10. As exemplarily illustrated, the capsules 14 may be spaced apart from each other along the periphery of the drug-retaining region 10. Accordingly, the capsules 14 may be considered as partially enclosing the periphery of the drug-retaining region 10. In another embodiment, however, the capsules 14 may contact each other along the periphery of the drug-retaining region 10 so as to completely enclose the periphery of the drug-retaining region 10. Referring to FIG. 2B the capsules 14 shown in FIG. 2A become degraded upon receiving energy in the manner described above with respect to FIG. 1B.

In one embodiment, the capsules 14 are disposed adjacent to a structure defining the periphery of the drug-retaining region 10. In another embodiment, the capsules 14 may be adhered to the structure defining the periphery of the drug-retaining region 10. In yet another embodiment, one or more of the capsules 14 may also be dispersed throughout the drug-retaining region 10 in the manner described above with respect to FIGS. 1A and 1B.

Figure 3A:
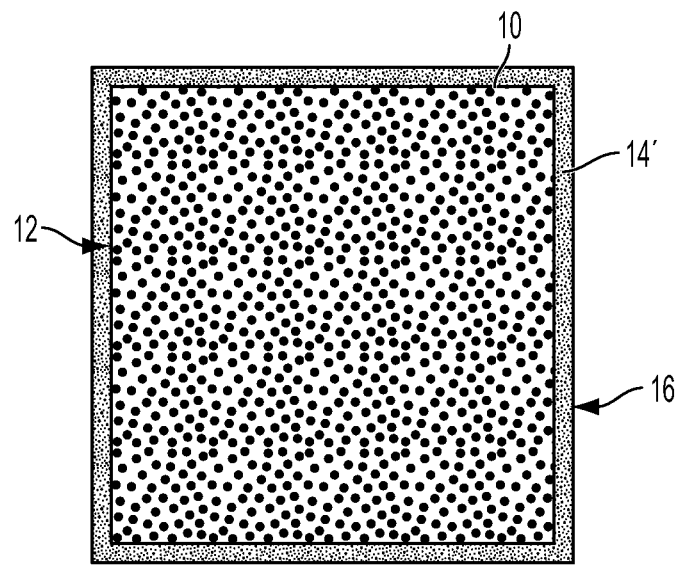
FIGS. 3A and 3B are plan views schematically illustrating another exemplary embodiment of a drug deactivation system according to another embodiment.
Figure 3B:
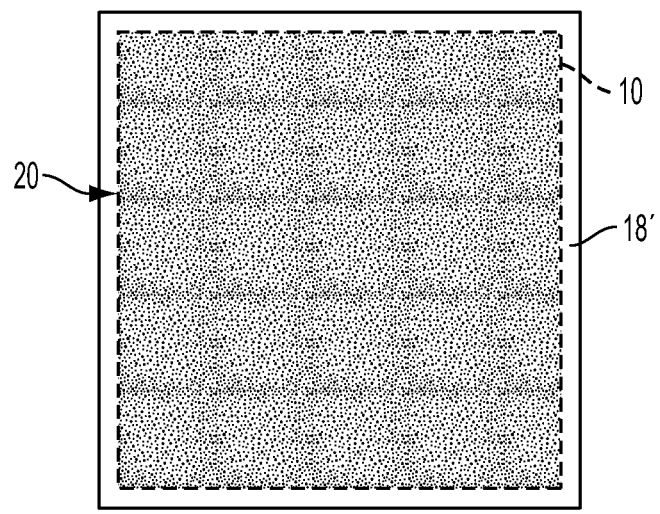

FIGS. 3A and 3B are plan views schematically illustrating an exemplary embodiment of a drug deactivation system according to another embodiment.

Referring to FIG. 3A, similar to the embodiment described above with respect to FIGS. 1A and 2A, a drug deactivation system may be implemented with a drug delivery device including a drug-retaining region 10 within which a drug 12 is retained. The drug deactivation system may include a single capsule 14' configured in a similar manner as exemplarily discussed above with respect to FIGS. 2A and 2B, but shaped to completely enclose the periphery of the drug-retaining region 10. In another embodiment, however, the single capsule 14' may partially enclose the periphery of the drug-retaining region 10. Referring to FIG. 3B the capsule 14' shown in FIG. 3A becomes degraded upon receiving energy supplied in a manner similar to that described with above respect to FIG. 2B.

In one embodiment, the capsule 14' is disposed adjacent to a structure defining the periphery of the drug-retaining region 10. In another embodiment, the capsule 14' may be adhered to the structure defining the periphery of the drug-retaining region 10. In yet another embodiment, one or more of the capsules 14 may also be dispersed throughout the drug-retaining region 10 in the manner described above with respect to FIGS. 1A and 1B.

According to the embodiment exemplarily described above with respect to FIGS. 3A and 3B, agent 16 is released into the drug 12 within the drug-retaining region 10 when the capsule 14' degrades, thereby rendering the drug 12 ineffective. Thus, as exemplarily described above, the drug 12 may be rendered ineffective when the agent 16 binds to the drug 12, when the agent 16 binds to receptors of the drug 12 or when the agent 16 chemically degrades the drug 12. In another embodiment, however, the drug 12 may be rendered ineffective when the drug 12 is physically incapable of being removed from the drug-retaining region 10. In such an embodiment, the agent 16 contained within the capsule 14' may be provided as a material (e.g., a polymer) capable of physically encapsulating the drug 12 within the drug-retaining region 12. For example, the capsule 14' may release a polymer capable of crosslinking upon exposure to moisture (e.g., a cyanoacrylate) or a polymer capable of crosslinking upon exposure to UV light (e.g., an epoxy). In one embodiment, polymer material of the agent 16 may further be capable of bonding to sidewalls of the drug-retaining region 10, thereby making extraction of the drug 12 difficult. In another embodiment, polymer material of the agent 16 may further be capable of penetrating into and/or encapsulating material forming the drug retaining region 10, thereby rendering the drug 12 inaccessible to chemical extraction mechanisms. In such an embodiment, the material forming the drug-retaining region 10 may be provided as a material such as a solid or gel having either nonporous or porous structures.

Figure 4A:
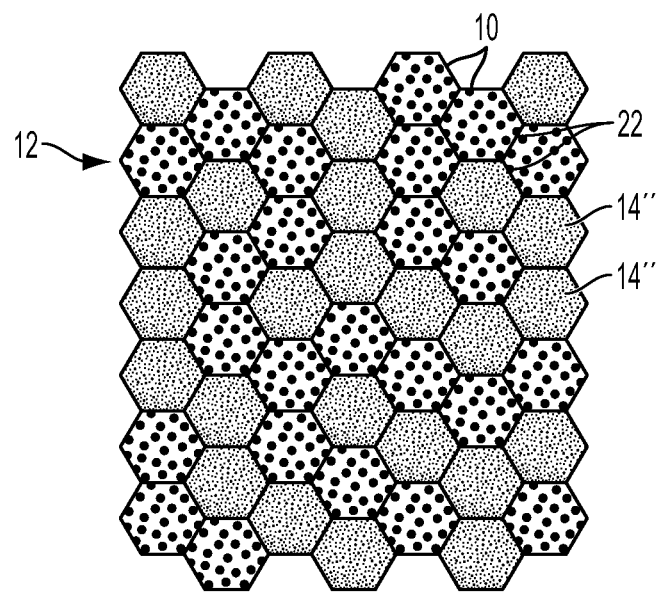
FIGS. 4A and 4B are plan views schematically illustrating another exemplary embodiment of a drug deactivation system according to another embodiment.
Figure 4B:
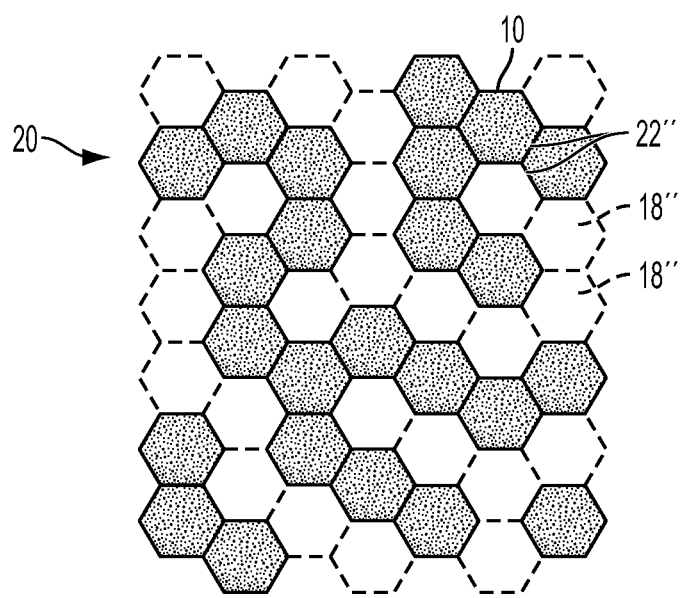

FIGS. 4A and 4B are plan views schematically illustrating an exemplary embodiment of a drug deactivation system according to another embodiment.

Referring to FIG. 4A, a drug deactivation system may be implemented with a drug delivery device including a plurality of drug-retaining regions 10 within which a drug 12 is retained. In the illustrated embodiment, the drug deactivation system may include a plurality of capsules 14" exposed to the plurality of drug-retaining regions 10. The capsules 14" may be configured as exemplarily discussed above with respect to FIGS. 1A and 1B. The capsules 14" may retain an agent 16 therein, which is also configured as exemplarily discussed above with respect to FIGS. 1A and 1B.

Collectively, the capsules 14" and the drug-retaining regions 10 may be arranged in an array within the drug-delivery device. However, as exemplarily illustrated, the capsules 14" and the drug-receiving regions 10 may be substantially randomly distributed within the array. In another embodiment, the capsules 14" and the drug-receiving regions 10 may be substantially regularly distributed within the array.

As exemplarily illustrated, the shape of each of the capsules 14 may be substantially the same as the shape of each of the drug-retaining regions 10. In another embodiment, however, at least one of the capsules 14 and at least one of the drug-retaining regions 10 may have substantially the same shape.

As exemplarily shown, some of the drug-retaining regions 10 are adjacent to one or more capsules 14" and some of the drug-retaining regions 10 are adjacent to one or more other drug-retaining regions 10. A membrane 22 may be interposed between adjacent ones of the drug-retaining regions 10. In one embodiment, each membrane 22 may comprise the same material as the capsules 14".

Referring to FIG. 4B the capsules 14" shown in FIG. 4A become degraded upon receiving energy in the manner described above with respect to FIG. 1B, thereby forming degraded capsules 18". In one embodiment, the capsules 14" shown in FIG. 4A become degraded upon receiving energy (e.g., chemical energy). In embodiments where the membrane 22 comprises the same material as the capsules 14", the membranes 22 may be also be degraded upon receiving energy, thereby forming degraded membranes 22". Agent 16 may be released from the capsules 14" and also be transferred through the degraded membranes 22".

According to the embodiments exemplarily described above with respect to FIGS. 1A-4B, the capsules 14, 14' and 14" contain agent 16 that is releasable into the drug 12, which is retained within the drug-retaining region 10, when the capsules are degraded. In another embodiment, however, the capsules 14, 14' and 14" may contain the drug 12 and the drug-retaining region 10 may retain the agent. In such an embodiment, the drug 12 may be released into agent 16 when the capsules 14, 14' and 14" are degraded. In one embodiment, drug 12 released from the degraded capsules may migrate within the agent 16 via self-diffusion or forced-diffusion (e.g., within a chemical gradient, a force gradient, an electrical potential gradient, or the like or a combination thereof).

As mentioned above, capsules may be degraded upon receiving energy from an energy source. Energy capable of degrading the plurality of capsules may include electrical energy, thermal energy, chemical energy, mechanical energy, electromagnetic radiation, magnetic energy, or the like or a combination thereof. In one embodiment, the energy source may be comprised as a part of the drug delivery device. In another embodiment, the energy source may be provided separately from the drug delivery device. For example, if the capsules described above are degradable in the presence of thermal energy such as heat, then the energy source could be a hair dryer supplied by the user of the drug retained within the drug-retaining region or somebody other than the user. In one embodiment, the energy may be supplied to the aforementioned capsules 14, 14' and 14" manually by the user of the drug 12 retained within the drug-retaining region 10 (or somebody other than the user). In another embodiment, the energy may be supplied to the aforementioned capsules 14, 14' and 14" automatically when a predetermined condition has been satisfied after detecting a characteristic of the user, a characteristic of the drug-retaining region, a characteristic of a user-engageable element of the drug delivery device, a characteristic of a region external to the drug delivery device and the user, or the like or a combination thereof. An exemplary discussion of such detection and automatic supplying of energy can be found in the aforementioned co-pending U.S. patent application Ser. No. 12/357,108 filed Jan. 21, 2009, now U.S. Pat. No. 7,838,715, entitled "DRUG DEACTIVATION SYSTEM AND METHOD OF DEACTIVATING A DRUG USING THE SAME."

As mentioned above, energy capable of degrading the capsules 14, 14' and 14" may include electrical energy. Various types of electrical energy may be may be applied to degrade the capsules 14, 14' and 14". In one embodiment, a localized electric current or electric field may be used to create a change in the solubility of the material from which the capsule is formed. The generation of reducing or oxidizing agents can significantly change local solubility. Capsules 14, 14' and 14" may be formed of a material such as polylactic-co-glycolic acid (PLGA), which is a biodegradable polymer that is insoluble in neutral to acidic pH conditions. By reducing the capsule's environment with a predetermined reduction reaction at a cathode, one can selectively increase the pH to promote PLGA solubility. Upon detection of a breach by the sensor, the agent 16 may be released when electrical energy is applied at the cathode. This causes a reduction reaction to occur, making the capsule's environment more basic and thereby increasing the solubility of the PLGA material of the capsules 14, 14' and 14". By increasing the solubility of the material from which the capsules 14, 14' and 14" are formed, the capsules 14, 14' and 14" may degrade by dissolving, thereby releasing the agent 16 into the drug-retaining region 10.

The solubility of the material from which the capsules 14, 14' and 14" are formed may also be changed in other ways. In another embodiment, the capsules 14, 14' and 14" may be fabricated using a bi-layer construction including an inner layer and an outer layer. The inner layer of each of the capsules 14, 14' and 14" may be soluble in the environment, and the outer layer may be normally insoluble in the environment. The outer insoluble layer may be dissolved by application of an electrical potential that oxidizes the outer layer. For example, an outer gold (Au) layer may be dissolved by the application of a voltage in the presence of a chloride solution (Au+4Cl-→AuCl4-+3e-(~1.1V, ~0.1 M chloride solution)). Once the outer Au layer is dissolved, the soluble inner layer is exposed to the environment and readily dissolves, releasing the agent 16 into the drug-retaining region 10.

Electrical energy may alternatively be applied to cause a change in gas pressure within the capsules 14, 14' and 14" that causes the capsules 14, 14' and 14" to degrade by rupture. For example, localized electrochemistry may be used to cause hydrolysis of water within the capsules 14, 14' and 14". By applying an electrical energy in the form of a voltage applied across the capsules 14, 14' and 14", a current is produced that breaks the water within the capsule into its constituent parts: hydrogen gas and oxygen gas. The gas pressure within the capsules 14, 14' and 14" is thereby increased, causing the capsules 14, 14' and 14" to degrade by rupture. The agent 16 is thereby released into the drug-retaining region 10, where it can mix with the drug 12 and render it ineffective.

As mentioned above, energy capable of degrading the capsules 14, 14' or 14" may include electromagnetic radiation. For example, the capsules 14, 14' and 14" may be composed of materials sensitive to various wavelengths of electromagnetic radiation such that, in the presence of a particular wavelength of electromagnetic radiation (e.g., microwave radiation, infrared radiation, visible light, ultraviolet radiation, or the like or a combination thereof), the capsules 14, 14' and 14" degrades. In one embodiment, the capsules 14, 14' and 14" may be formed of a polymer material capable of absorbing light in the infrared range. The capsule material could then be heated directly by a source of electromagnetic radiation (e.g., microwave radiation, infrared radiation, visible light, ultraviolet radiation, or the like or a combination thereof) coupled to the drug delivery device. In one embodiment, the source of electromagnetic radiation may include an infrared light source (e.g., an aluminum-gallium-arsenic light emitting diode) coupled to the drug delivery device. In another embodiment, the capsules 14, 14' and 14" may be formed of a material that is relatively insensitive to light in the infrared range, but be coated with a supplemental coating capable of absorbing light in the infrared range. The capsule material could then be heated indirectly by the infrared light source via the supplemental coating. When the capsule material is sufficiently heated, a phase change (e.g., melting or vaporization) within the capsule material occurs and the capsule 14, 14' or 14" is degraded to release the agent 16.

In another embodiment, the agent 16 itself may be sensitive to particular wavelengths of electromagnetic radiation (e.g., microwave radiation, infrared radiation, visible light, ultraviolet radiation, or the like or a combination thereof). Accordingly, one or more light sources configured to emit light at one or more of the particular wavelengths of light may be coupled to the drug delivery device. While the example of an infrared light source and a capsule material or coating sensitive to infrared light is given, a person of skill in the art will recognize that any combination of electromagnetic radiation source and capsule material/coating/agent sensitive to that wavelength may be used.

As mentioned above, energy capable of degrading the capsules 14, 14' or 14" may include thermal energy. In an exemplary embodiment, thermal energy may be supplied to the capsules 14, 14' and 14" using one or more heating elements disposed on the inside or the outside of the capsules 14, 14' and 14". In one embodiment, a heating element may be provided as a resistive heaters (e.g., patterned resistors). The patterned resistors may be used for resistive ($I^2R$) heating, causing the material from which the capsule is formed to degrade by either thermal stress due to rapid heating or cooling (e.g., thermal shock, thermal stress due to thermal expansion coefficient mismatch or stresses induced due to volumetric changes associated with phase changes). If the capsule material has a high coefficient of thermal expansion and is brittle, rapid heating may also cause the capsule to degrade by fracture, so that the capsule is cracked open. The agent 16 is thereby released into the drug-retaining region 10, allowing it to mix with the drug 12 and render the drug 12 ineffective.

In another embodiment, thermal energy may be applied to induce a phase change (e.g., via boiling, vaporizing, etc.) within the agent 16 itself, causing the agent 16 to transition from a liquid phase to a gaseous phase. In such an embodiment, the internal pressure within the capsule 14, 14' or 14" increases, causing the capsule 14, 14' or 14" to degrade by rupture. Upon rupture, the agent 16 is released into the drug-retaining region 10, where it can combine with the drug 12 and render the drug ineffective. In another embodiment, the capsule 14, 14' or 14" may contain a secondary chemical that may undergo a phase change sufficient to rupture the capsule 14, 14' or 14". Accordingly, the capsule 14, 14' or 14" may be ruptured due to the phase change of the secondary chemical instead of (or in addition to) the agent 16.

As mentioned above, energy capable of degrading the capsules 14, 14' or 14" may include chemical energy. For example, in the drug deactivation system exemplarily described above with respect to FIGS. 4A and 4B, the capsules 14" and/or the membranes 22 may be degraded by a chemical reaction such as dissolution when, for example, the drug delivery device is immersed in water or other solution or solvent.

As mentioned above, energy capable of degrading the capsules 14, 14' or 14" may include mechanical energy. For example, in the drug deactivation system exemplarily described above with respect to FIGS. 4A and 4B, the capsules 14" and/or the membranes 22 may be degraded by being mechanically separated from each other when, for example, the drug delivery device is immersed in water or other solution or solvent. Upon being mechanically separated from each other, the agent 16 mixes with the drug 12, thereby rendering the drug 12 ineffective.

In another example, the drug delivery device may include a spring-loaded piercing mechanism housed in the drug delivery device, which can degrade (i.e., pierce) the capsule 14, 14' or 14" when the spring is released. This mechanical force releases the agent 16 from the capsule 14, 14' or 14" and into the drug-retaining region 10, where it combines with the drug 12 and renders it ineffective.

Alternatively, acoustic energy may be focused on the capsules 14, 14' or 14". In this manner, the acoustic force operates as a mechanical energy which ruptures or otherwise degrades the capsule 14, 14' or 14". For example, an acoustic source may be integrated onto the backside of the capsule 14, 14' or 14", or at a periphery of the drug-retaining region 10. The acoustic energy source may be activated to degrade the capsules 14, 14' or 14" and release agent 16 into the drug-retaining region 10. Lens designs can be used to focus the acoustic energy as an acoustic force on the capsule 14, 14' or 14", thereby imparting a mechanical energy on the capsule 14, 14' or 14" to rupture or otherwise degrade the capsule 14, 14' or 14". If the acoustic energy is focused over a large depth of field, multiple capsules 14, 14' or 14" may be ruptured or otherwise degraded simultaneously.

As mentioned above, energy capable of degrading the capsules may include magnetic energy. For example, the capsules 14, 14' or 14" may have magnetic shape memory (MSM) alloys incorporated therewith. MSM alloys are smart materials which can undergo large reversible deformations in an applied magnetic field, for example, $Ni_2MnGa$. By incorporating these MSM materials with the capsule 14, 14' or 14", the capsule 14, 14' or 14" may be capable of undergoing critical strains and stresses when a magnetic field is applied, allowing the capsule 14, 14' or 14" to degrade through rupturing or cracking.

According to the embodiments exemplarily described above with respect to FIGS. 1A-4B, energy is applied to one or more capsules 14, 14' or 14" to degrade the capsules 14, 14' or 14". When the capsules 14, 14' or 14" are degraded, an agent 16 is provided to render a drug 12 ineffective. Thus, the drug 12 may be rendered ineffective when energy is applied to one or more capsules 14, 14' or 14". In other embodiments, however, the drug 12 may be rendered ineffective without the need for any capsule 14, 14' or 14". For example, a drug deactivation system may include at least one energy source configured to transmit energy (e.g., electrical energy, electromagnetic energy, thermal energy, or the like or a combination thereof) to the drug 12 retained within the drug-retaining region 10. Upon receiving the energy, the drug 12 is rendered ineffective. Exemplary drug deactivation systems according to such embodiments, will now be discussed with reference to FIGS. 5 and 6.

Figure 5:
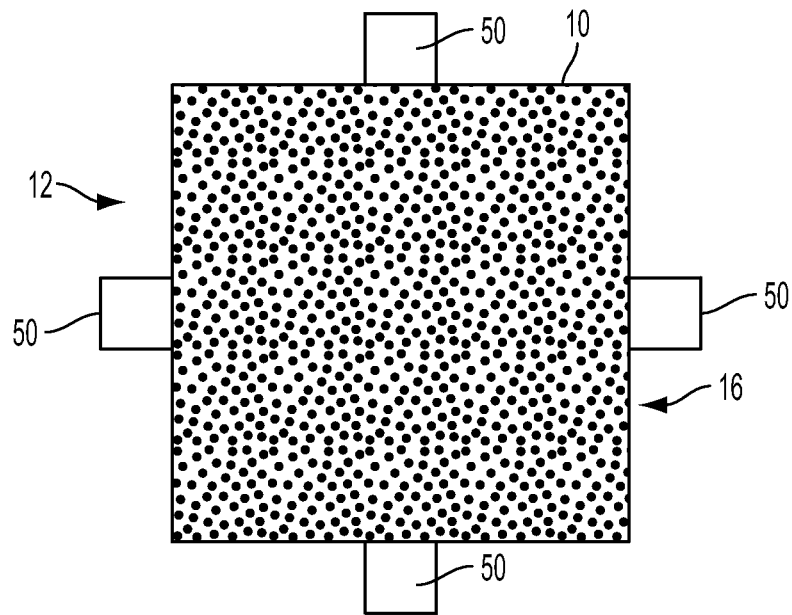
FIG. 5 is a plan view schematically illustrating a drug deactivation system according to another embodiment.

Referring to FIG. 5, a drug deactivation system may include plurality of energy sources 50 coupled to the drug-retaining region 10. In one embodiment, the energy sources 50 may be disposed within a housing of the drug delivery device, along with the drug-retaining region 10. The energy sources 50 may be configured to transmit energy to the drug 12 retained within the drug-retaining region 10 to render the drug 12 ineffective. Although FIG. 5 illustrates a four energy sources 50 disposed approximately equidistant from each other, it will be appreciated that any number of energy sources 50 (i.e., one or more) may be used and arranged as desired.

In one embodiment, one or more energy sources 50 may be configured to apply mechanical energy (e.g., in the form of acoustic waves) to the drug 12 retained within the drug-retaining region 10 to render the drug 12 ineffective. For example, one or more energy sources 50 may be provided as an ultrasonic transducer disposed in communication with the drug 12 retained within the drug-retaining region 10 to generate acoustic waves within the drug 12. In embodiments where the drug 12 is rendered ineffective upon the application of acoustic waves, the drug 12 may, for example, be capable of undergoing an irreversible phase transformation to become crystallized. When the drug 12 is crystallized, the drug 12 is converted to an insoluble form and is, therefore, ineffective to the user. In another example, acoustic waves generated by one or more energy sources 50 may generate ultrasonic waves within the drug 12 and heat the drug 12. When the drug 12 is sufficiently heated, the drug 12 is rendered ineffective within the drug-retaining region 10. In one embodiment, the ultrasonic waves generated may both crystallize and heat the drug 12 within the drug-retaining region 10.

In one embodiment, one or more energy sources 50 may be configured to apply electrical energy to the drug 12 retained within the drug-retaining region 10 to render the drug 12 ineffective. Accordingly, one or more energy sources 50 may be provided as electrodes (e.g., carbon electrodes) disposed in electrical communication with the drug 12 retained within the drug-retaining region 10. Upon applying a sufficient voltage to the electrodes, the drug 12 may undergo an electrochemical reaction to produce hydrogen peroxide ($H_2O_2$). The $H_2O_2$ may then oxidize the drug 12 within the drug-retaining region 10. Other possible oxidizing agents that could be created electrochemically include OH. radicals formed from water molecules and hypochlorite electrogenerated from any chloride ions of the drug 12. In another example, either the drug 12 itself may dissociate or a drug matrix associated with the drug 12 may undergo electrolysis, wherein the free oxygen or hydrogen gas produced by the electrolysis may render the drug 12 ineffective.

Figure 6:
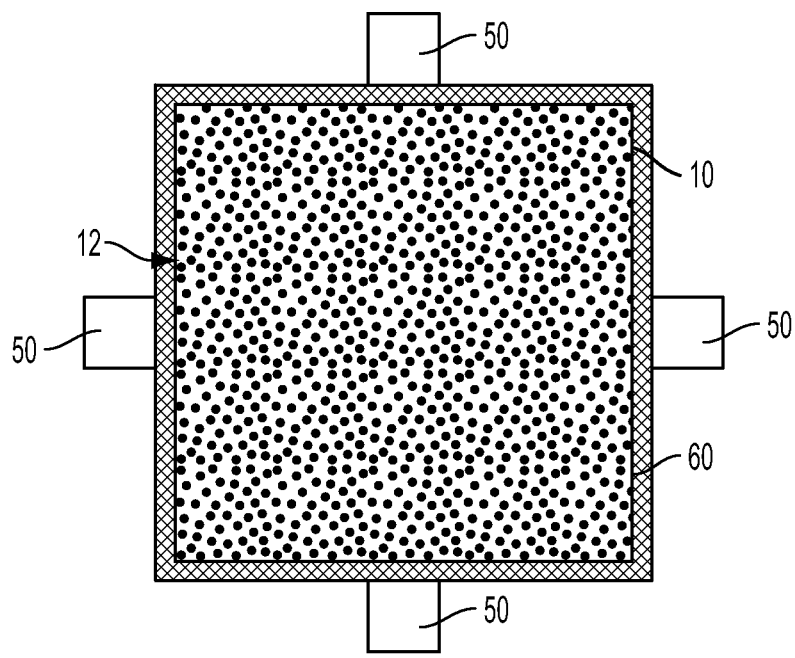
FIG. 6 is a plan view schematically illustrating a drug deactivation system according to another embodiment.

Referring to FIG. 6, a drug deactivation system may further include an absorbing element 60 disposed within the drug-retaining region 10. Each of the energy sources 50, as similarly described above with respect to FIG. 5, may be provided as an electrode electrically connected to the absorbing element 60. The absorbing element 60 is configured to absorb the drug 12 in the presence of a voltage applied from the electrodes. When the drug 12 is absorbed by the absorbing element 60, release of the drug 12 from within the drug-retaining region 10 can be significantly or completely prevented. In one embodiment, the absorbing element 60 may be provided as an activated carbon network (e.g., an activated carbon fabric) disposed within the drug-retaining region 10. Although FIG. 6 illustrates wherein the absorbing element 60 completely surrounds the periphery of the drug-retaining region 10, it will be appreciated that the absorbing element 60 may partially surround the periphery of the drug-retaining region 10. It will also be appreciated that a plurality of absorbing elements 60 may be provided, each connected to the same or to different electrodes.

In embodiments where the drug 12 is a cationic drug, a positive voltage, (e.g., about +0.1V to about +0.5 V) may be applied from the electrodes to the absorbing element 60 to prevent absorption of the drug 12 during normal use. However, if a predetermined condition has been satisfied after detecting a characteristic of the user, a characteristic of the drug-retaining region, a characteristic of a user-engageable element of the drug delivery device, a characteristic of a region external to the drug delivery device and the user, or the like or a combination thereof, the electrodes may discontinue applying the voltage to the absorbing element 60, or may reverse the polarity of the voltage applied to the absorbing element 60. Upon discontinuing application of, or reversing the polarity of, a voltage to the absorbing element 60, the drug 12 is absorbed by the absorbing element 60 and is thereby rendered ineffective. In embodiments where the drug 12 is an anionic drug, voltages of opposite polarities would be applied to the absorbing element 60.

Referring back to FIG. 5, one or more energy sources 50 may be configured to apply electromagnetic radiation (e.g., microwave radiation, infrared radiation, visible light, ultraviolet radiation, or the like or a combination thereof) to the drug 12 retained within the drug-retaining region 10 to render the drug 12 ineffective. For example, one or more energy sources 50 may be provided as a light-emitting element (e.g., an LED) disposed in optical communication with the drug 12 retained within the drug-retaining region 10. In embodiments where the drug 12 is rendered ineffective upon the application of ultraviolet light, the drug 12 may include a material such as an alcohol.

In yet another embodiment, one or more energy sources 50 may be configured to apply thermal energy (i.e., heat) to the drug 12 retained within the drug-retaining region 10 to render the drug 12 ineffective. In one embodiment, one or more energy sources 50 may be provided as a light-emitting element (e.g., an LED) disposed in optical communication with the drug 12 retained within the drug-retaining region 10 and be capable of emitting electromagnetic radiation suitable for heating the drug 12 within the drug-retaining region 10. In another embodiment, one or more energy sources 50 may be provided as a heating element (e.g., a resistive heater) disposed on the inside or the outside of the drug-retaining region 10. In embodiments where the drug 12 is rendered ineffective upon the application of heat, the drug 12 may be a protein-based drug.

It will be appreciated that several of the above-disclosed and other features and functions, or alternatives thereof, may be desirably combined into many other different systems or applications. It will also be appreciated that various presently unforeseen or unanticipated alternatives, modifications, variations, or improvements therein may be subsequently made by those skilled in the art which are also intended to be encompassed by the following claims.

What is claimed is:

1. A method of deactivating a drug, the method comprising:
   retaining a drug within a drug-retaining region of a drug delivery device, wherein the drug is capable of being rendered ineffective in the presence of the transmitted energy; and
   transmitting energy to the drug retained within the drug-retaining region of the drug delivery device.

2. The method of claim 1, wherein transmitting the energy includes transmitting at least one type of energy selected from the group consisting of mechanical energy, electrical energy, thermal energy, and electromagnetic radiation.

3. The method of claim 2, wherein transmitting the energy comprises transmitting at least one type of electromagnetic radiation selected from the group consisting of microwave radiation, infrared radiation, visible light and ultraviolet radiation.

4. The method of claim 2, wherein transmitting the energy comprises:
   transmitting electrical energy to an absorbing element contacting the drug; and
   absorb at least a portion of the drug retained within the at least one drug-retaining region in the presence of the transmitted electrical energy.

5. The method of claim 2, wherein transmitting the energy comprises transmitting ultrasonic energy.

6. The method of claim 5, wherein the ultrasonic energy is configured to crystallize the drug, heat the drug or a combination thereof.

* * * * *